United States Patent [19]

Goof et al.

[11] Patent Number: 4,580,562
[45] Date of Patent: Apr. 8, 1986

[54] ELECTROSURGICAL APPARATUS

[76] Inventors: Sven K. L. Goof, Gl. Strandvej 236 A, DK-3050 Humlebaek; Jens S. Hansen, Hjortevaenget, DK-2980 Kokkedal, both of Denmark

[21] Appl. No.: 617,846

[22] Filed: Jun. 7, 1984

Related U.S. Application Data

[63] Continuation of Ser. No. 336,295, Dec. 13, 1981, abandoned.

[30] Foreign Application Priority Data

Jan. 2, 1981 [DK] Denmark .................................. 15/81

[51] Int. Cl.⁴ ............................................. A61B 17/39
[52] U.S. Cl. ................................................ 128/303.14
[58] Field of Search ...................... 128/303.13, 303.14, 128/303.17, 303.18, 303.15

[56] References Cited

U.S. PATENT DOCUMENTS

| | | | |
|---|---|---|---|
| 3,315,678 | 4/1967 | Donelson | 128/303.18 |
| 3,707,149 | 12/1972 | Hao et al. | 128/303.19 X |
| 3,875,945 | 4/1975 | Friedman | 128/303.17 X |
| 3,999,552 | 12/1976 | Huggins | 128/303.13 |
| 4,092,986 | 6/1978 | Schneiderman | 128/303.14 |
| 4,321,926 | 3/1982 | Roge | 128/303.18 |

FOREIGN PATENT DOCUMENTS

| | | | |
|---|---|---|---|
| 2383675 | 11/1978 | France | 128/303.13 |
| 1513057 | 6/1978 | United Kingdom | 128/303.13 |

OTHER PUBLICATIONS

"The Feed-Backs of Servotome", pp. 1-4.

Primary Examiner—Lee S. Cohen
Attorney, Agent, or Firm—Fleit, Jacobson, Cohn & Price

[57] ABSTRACT

An electrosurgical apparatus comprises a high frequency power generator, a high frequency transformer, a handpiece for mounting an electrode, and a connecting cable between the generator and the handpiece. In order to provide an automatic adaptation or adjustment so that the power delivered by the cutting electrode is continuously changed according to the cutting depth, the effective length of the connecting cable has been adapted to the output frequency of the generator so that the transfer characteristic of the cable provides a true ohmic transfer or reflection of the load at the electrode-end of the cable to the generator-end of the cable.

6 Claims, 2 Drawing Figures

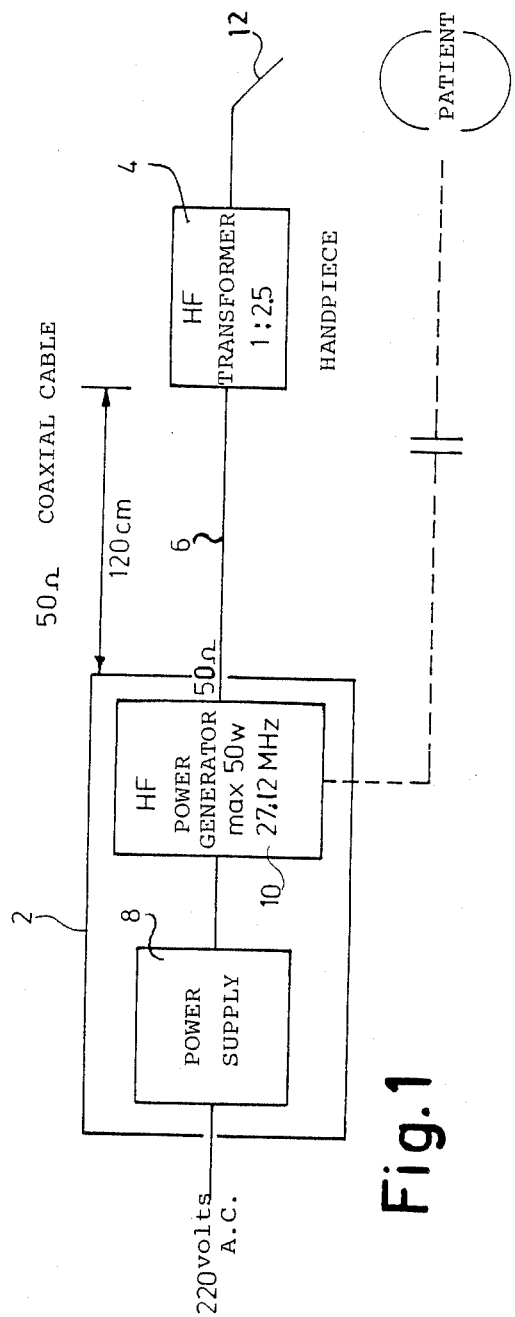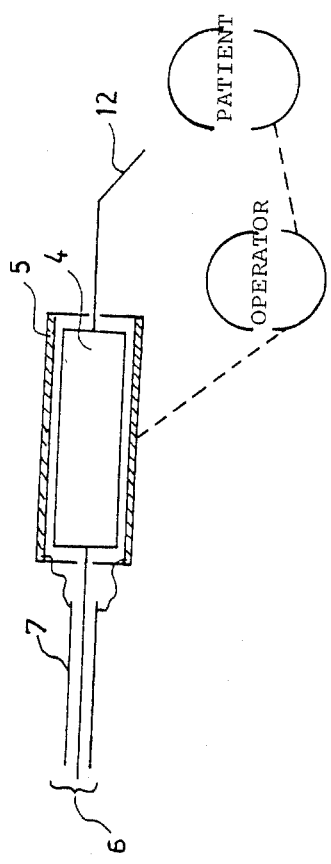

ELECTROSURGICAL APPARATUS

This application is a continuation of application Ser. No. 336,295, filed Dec. 13, 1981, now abandoned.

BACKGROUND OF THE INVENTION

The present invention relates to an electrosurgical apparatus of the type comprising a high frequency power generator, a high frequency transformer, a handpiece for mounting an electrode, and a connection wire between the generator and the handpiece. Such apparatuses are used in particular by surgeons and dentists to perform incisions and also to stop bleeding.

In electrosurgical equipment of the type in question, a high frequency current is conducted through a relatively thin, wire-shaped electrode which remains cold because of good conductivity, but when the electrode is moved through tissue, heat is generated, a.o. because of the electrical resistance of the tissue. This causes a molecular dissolution of the tissue cells, since the generated heat causes both intra- and extracellular generations of steam which bursts the tissue. How deep in the tissue this dissolution takes place, depends on the intensity of the current and on the speed at which the electrode is moved through the tissue.

An important advantage of such an electrode dissection instead of using a scalpel resides in the fact that the operating area is free from bleeding. This is an important advantage in connection with the taking of impressions for tooth crowns and bridges, as an impression may be taken immediately after the necessary incisions have been made. Electro-surgery is also well suited for preposthetic surgery and paradontal surgery.

Electrosurgical equipment has, however, not yet gained the extended use which the important advantages should justify. This is due to several substantial drawbacks. Thus, it is difficult to use the apparatus or its electrode in a correct manner. If the electrode is kept still, the destruction of tissue will become very extensive and may result in periostitis, bone tissue necrosis and sequestrian of bone tissue. With too high electrode voltage or, if the electrode is moved too slowly through the tissue, permanent and very painful damages may be done to bone tissue and also to tooth substances. For the time being, the use of electrosurgery is therefore deprecated, when the electrode may approach or get in contact with bone tissue, and this is a substantial and unfortunate limitation of the possibilities of use.

Another considerable disadvantage consists in the fact that it is difficult to control the power output of the apparatus in a sufficiently effective and precise way. When cutting with the electrode of the apparatus, the necessary or desired output power varies with the depth of the cut, with the impedance provided by the patient, and with numerous other factors relating to the shape of the electrode, the environment and the particular operating procedure. This has had the effect that prior electrosurgical apparatuses have been provided with several adjustments for manually presetting the power output, such as a pre-adjustment for each electrode belonging to the apparatus, whereby a desired output power may be selected, usually by adjusting the output voltage.

U.S. Pat. No. 4,092,986 discloses an electrosurgical unit of the type contemplated which includes an inverse feed-back circuit to maintain the output voltage level from the unit at a substantially constant value independent of the load.

However, when the output voltage is applied to a patient by means of the electrode, the patient will act as a load which causes that the output voltage level decreases. The magnitude of the load or of the voltage decrease depends on the electrical resistance of the tissue in which the cut is being made and of the instantaneous depth of the cut. Thus, the load resistance decreases as a function of the cutting depth and, moreover, the load resistance depends on the type of tissue which the electrode is encountering. Accordingly, a continuous regulation is necessary as the load is changing, and the voltage delivered by the electrode should not be constant.

Another commercially available electrosurgical apparatus comprises a double feed-back circuit and a data analyser to maintain an electrode output voltage level which is automatically and continuously adapted to the electrical tissue resistance and to the variations in the depth of the cut so that the power delivered by the cutting electrode currently is proportional with the cutting depth. However, the electronics of the apparatus introduce time constants and, accordingly, it will be difficult to obtain a sufficient quickness in the adaptation or regulation.

SUMMARY OF THE INVENTION

It is, accordingly, an object of the invention to provide an electrosurgical apparatus which continuously and effectively regulates or adapts the power output depending on the instantaneous load resistance without employing complicated feed-back circuits with associated time constants and delays in the regulation.

This is obtained by the apparatus of the invention which is characterized by the length of the connecting wire being adapted to the output frequency of the generator in such a manner that the transfer characteristic of the connecting wire provides a substantially true ohmic transfer of loads at the electrode-end of said wire to the generator-end of said wire about and at least in a balance point.

Prior art electrosurgical apparatuses have also been insufficient with respect to an adequately effective electrical coupling or adaptation between the patient and the generator of the apparatus. The generator corresponds to a radio transmitter and the power seeks to move from the electrode, through the tissue of the patient and then through the environment back to the generator.

In order to avoid that the return path excessively weakens the energy, it is therefore important that the return path is made as effective as possible. In prior art apparatuses, this takes place by using a passive return electrode which is coupled to the patient, and a return wire which extends back to the generator.

Such a passive electrode with return wire is an inconvenient arrangement which under unfortunate circumstances may result in burnings on the skin of the patient, and is not necessary in an embodiment of the apparatus of the invention which is characterized by the output frequency of the generator being in the order of 15-30 megahertz and by the transformer being located at the electrode-end of the connecting wire and included in the handpiece of the apparatus. The high generator frequency combined with the particular location of the transformer results in a low impedance, in an effective impedance matching to the environments, and in an effective return path between patient and generator. Moreover, an improved and more acurate cutting is achieved together with and almost sparkless operation. In prior art apparatuses the frequency is about ten times lower and the transformer is included in the same housing as the generator.

In addition, the substantially higher frequency is particularly advantageous in the apparatus of the invention since the particular, adapted length of the connecting wire or cord which depends on the wave length and thereby on the frequency, will be a convenient length which can be used without any further arrangements. Moreover, the high frequency contributes to the effectiveness of the cutting effect due to the dielectric (polarization) losses which the frequency provides in the tissue.

BRIEF DESCRIPTION OF THE DRAWINGS

In the following, the present invention will be described in further detail referring to the drawing in which, FIG. 1 is a schematic diagram illustrating an embodiment of the electrosurgical apparatus of the invention, FIG. 2 is a schematic view illustrating an alternative embodiment including particular return path means.

DESCRIPTION OF THE PREFERRED EMBODIMENTS

The apparatus of the invention illustrated in FIG. 1 comprises an apparatus housing 2, a handpiece 5 and a connecting wire or cord 6 extending between the housing and handpiece of the apparatus. The housing includes a power supply 8 which is adapted for connection to usual 220 volt AC mains. The power supply is connected to a high frequency power generator 10 which in the preferred embodiment illustrated has a maximum output power of 50 watts and an output frequency of 27.12 megahertz which is within a permissible frequency range. The generator operates approximately as a steady current generator.

The handpiece 4 includes a high frequency transformer which in the embodiment illustrated has a transformation ratio of 1:2.5. The handpiece is provided with equipment for replaceably connecting electrodes 12 thereto, generally in the shape of thin wire electrodes which can be bent in various shapes in view of the employment contemplated. Other special electrode configurations may also occur, in particular for stopping bleeding.

The handpiece 4 and the output of the generator 10 are connected through the connecting cord 6. In the preferred embodiment illustrated, this cord is a 50 ohm coaxial cable having a length of 120 cm. This length is matched to a quarter of a wave length, measures being taken, however, in order to compensate for the effect that the equipment, in particular the transformer, influences on the effective length of the cable.

With the particular values shown in FIG. 1 and mentioned above, the specially adapted cable 6 results in a true ohmic transfer or reflection of a 50 ohm load resistance at the electrode or transformer end of the cable into a load of 50 ohm at the generator end of the cable. As an example, a doubling of the load resistance at the electrode end will result in a halving of the load at the generator end in and about this balance point at 50 ohm.

A very quick regulation of this type is absolutely necessary in connection with electrosurgery, and the defectiveness of prior art electrode surgical apparatuses in that respect has been the reason why it is presently deprecated to use electrosurgery for incisions whereby the cutting electrode may contact or approach bone tissue.

Soft tissue has an electrical resistance which is substantially less than that of bone tissue due to the larger liquid contents of soft tissue. If a cutting electrode is advanced through soft tissue, a rather sudden increase will occur in the load resistance of the electrode when the electrode approaches bone tissue. Therefore, it is extremely necessary that the cutting power delivered by the electrode be reduced practically momentarily when the tissue resistance increases. Otherwise the result will be bone necrosis and sequestration of bone tissue which are very painful to the patient.

If the cutting depth is suddenly decreased when making a cut in soft tissue, a sudden increase in the load resistance of the electrode will also occur, and again it is necessary that a very quick reduction takes place in the cutting power since otherwise the result will be a serious burning in the tissue.

In connection with electrosurgery it is, accordingly, extremely important that the power delivered by the cutting electrode is automatically regulated in an acurate and very quick manner depending on the instantaneous load resistance of the electrode.

The apparatus of the invention provides such a automatic regulation of the cutting power which is continuously maintained inversely proportional to the instantaneous load resistance and, accordingly to the type of tissue and/or the cutting depth. The power regulation in the apparatus of the invention takes place without time delays, and the risk of damages to bone tissue and of burning of soft tissue is therefore reduced very considerably. This is achieved due to the matching or adaptation of the connection cable and entirely without complicated feed-back circuits which would include time constants and, accordingly, would cause delays in the regulation. The embodiment illustrated operates very effectively, but experiments have shown that a reduction of only 10 cm of the connecting cable 6 results in the apparatus not operating at all. Accordingly, the cable length is a decisive factor.

With correctly adapted cable length the automatic power regulation is very effective and rapid, and it is not necessary to make manual pre-settings in connection with replacements of the cutting electrode 12 such as is the case in several prior art apparatuses.

The impedance matching to the environment is very effective and influences from external foreign fields are excluded.

In FIG. 1, the return path from the patient and back to the generator 10 is indicated with dotted lines, since a separate return conductor is not necessary as in prior art apparatuses using substantially lower frequencies and in which the transformer is located at the generator end of the connecting cable.

FIG. 2 of the drawing illustrates an embodiment of the apparatus of the invention in which a particularly effective return path has been provided by connecting the shield conductor 7 of the coaxial connecting cable 6 with a tubular mantle or casing 5 made of an electrically conducting material and surrounding the handpiece 4 or at least the portion thereof being adapted to be held and grasped in the hand of the operator. Preferably, the tubular mantle 5 is provided with a relatively thin exterior layer or liner of an insulating material.

As indicated in FIG. 2, the operator of the apparatus will form part of the return path when manipulating the handpiece of the apparatus in one hand while touching the patient with the other hand. From the mantle 5 and back to the generator 10, the return path extends through the shield conductor 7 of the connecting cable 6. Accordingly, an effective and improved return path has been provided in this manner.

As mentioned above, the effective length of the connecting cable is preferably adapted to one quarter of the wave length. However, the cable length may also be adapted to other appropriate fractions or multiples of the wave length such as one half of the wave length.

Many different arrangements may be made within the broad scope of the invention, and it is to be appreciated that the invention is not to be limited to the specific examples given. The scope of the invention should be determined only as limited by a proper interpretation of the terms used in the following claims.

We claim:

1. An electrosurgical apparatus comprising:
   a high frequency power generator having an output frequency of the order of 15 to 30 megahertz,
   a handpiece including electrode mounting means for replaceably mounting an electrode thereon,
   a connecting wire connected between said generator and said handpiece,
   a high frequency transformer, said generator, said connecting wire and said transformer being connected to provide power to said electrode mounting means of said handpiece and to an electrode mounted therein, the length of the connecting wire being so adapted to the output frequency of said generator that the transfer characteristic of said connecting wire provides a substantially true ohmic transfer of loads on an electrode mounted on said electrode mounting means to the generator in and about a balance load point to provide automatic regulation of power delivered to tissue being cut by the electrode in response to the instantaneous load resistance experienced by the electrode.

2. An apparatus as defined in claim 1, wherein said transformer is included in said handpiece.

3. An apparatus as defined in claim 2, wherein said connecting wire is a shielded conductor of a coaxial cable, the shielding conductor of said coaxial cable being electrically connected to a tubular casing of electrically conducting material, said tubular casing surrounding at least a part of said handpiece.

4. An apparatus as defined in claim 2, wherein the effective length of said connecting wire is adapted to one quarter of a wave length of the output frequency of said generator.

5. An apparatus as defined in claim 1, wherein said connecting wire is a shielded conductor of a coaxial cable, the shielding conductor of said coaxial cable being electrically connected to a tubular casing of electrically conducting material, said tubular casing surrounding at least a part of said handpiece.

6. An apparatus as defined in claim 1, wherein the effective length of said connecting wire is adapted to one quarter of a wave length of the output frequency of said generator.

* * * * *